(12) United States Patent
Betageri

(10) Patent No.: US 6,627,647 B1
(45) Date of Patent: Sep. 30, 2003

(54) SUBSTITUTED 1-(4-AMINOPHENYL) IMIDAZOLES AND THEIR USE AS ANTI-INFLAMMATORY AGENTS

(75) Inventor: Rajashekhar Betageri, Bethel, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/533,207

(22) Filed: Mar. 23, 2000

(51) Int. Cl.[7] ............... A61K 31/4439; C07D 401/14
(52) U.S. Cl. .............. 514/333; 546/256; 514/399; 548/338.1
(58) Field of Search ............... 546/256; 514/333

(56) References Cited

U.S. PATENT DOCUMENTS 4,301,169 A   11/1981   Yamanaka et al.

FOREIGN PATENT DOCUMENTS

| WO | WO-9502591 A1 | 1/1995 |
| WO | WO-9603388 A1 | 2/1996 |
| WO | WO 99/28317 | * 6/1999 |

* cited by examiner

Primary Examiner—Patricia L. Morris
(74) Attorney, Agent, or Firm—Robert P. Raymond; Timothy X. Witkowski; Anthony P. Bottino

(57) ABSTRACT

A compound of Formula Ia

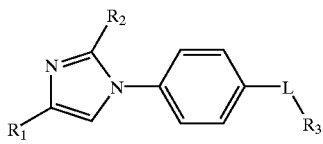

Ia wherein:

$R_1$ and $R_2$, which are the same or different, are $CF_3$; halogen; CN; branched or unbranched $C_{1-8}$ alkyl; branched or unbranched $C_{1-8}$ alkenyl; $C_{3-8}$ cycloalkyl optionally substituted with OH, CN, or methoxy; $C_{1-8}$ alkoxy; $C_{1-4}$ alkyloxyalkyl; $C_{1-8}$ alkylthio; $C_{1-4}$ alkylthioalkyl; $C_{1-8}$ dialkylamino; $C_{1-4}$ dialkylaminoalkyl; $CO_2R_4$ where $R_4$ is $C_{1-4}$ alkyl or $C_{1-4}$ alkenyl optionally substituted with carbocyclyl or heterocyclyl; or aryl or heterocyclyl connected to the imidazole in any position that makes a stable bond wherein the aryl or the heterocyclyl thereof is optionally substituted with halogen, $C_{1-4}$ alkyl, $C_{1-4}$ alkenyl, CN, $Me_2N$, $CO_2Me$, OMe, aryl, heterocyclyl, or $R_4$;

L is —NHC(O)—; —NHC(O)O—; —NHC(O)C(O)—; —NHC(S)—; —NH—; —NHC(O)NH—; —NHC(S)NH—; —NHCH$_2$—; —NHCH($R_5$)—, wherein $R_5$ is H, CN, $C_{1-6}$ alkyl, $C_{1-6}$ alkyloxyalkyl, $C_{1-6}$ alkylthioalkyl, $C_{1-6}$ alkylsulfinylalkyl, $C_{1-6}$ alkylsulfonylalkyl, $C_{3-6}$ cycloalkyl, heterocyclyl, or aryl optionally substituted with a halogen, $C_{1-4}$ alkyl, CN, $Me_2N$, $CO_2Me$, or OMe; or —NHC($R_5$)-lower alkyl; and $R_3$ is $C_{1-8}$ alkyl; $C_{1-8}$ alkyloxy; $C_{1-8}$ alkylthio; $C_{1-8}$ alkylamino; $C_{1-4}$ alkoxyalkyl; $C_{1-4}$ alkylthioalkyl; $C_{1-4}$ alkylaminoalkyl; $C_{1-4}$ dialkylaminoalkyl; —$CO_2R_6$; —$N(R_6)_2$; —$NH(R_6)$; —$C(O)R_6$; —$OR_6$; $S(O)_nR_6$, wherein n is 0, 1, or 2; —$SO_2NHR_6$; —$SO_2N(R_6)_2$; or carbocyclyl or heterocyclyl, wherein the carbocyclyl or heterocyclyl thereof is optionally substituted with one or more of the following: halogen, —CN, —$NO_2$, —$SO_2NH_2$, $CF_3$, $OCF_3$, $OC_{1-4}$alkyl, $OC_{3-5}$alkenyl, $CO_2C_{1-2}$alkyl, SMe, $NMe_2$, $R_6$, or $O(CH_2)_pR_7$, where p is 3 or 4 and $R_7$ is CN, $CO_2Me$, 2-(1,3-dioxolanyl), OH, or $OC_6H_5$;

wherein:

$R_6$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-6}$ alkylthioalkyl, $C_{1-6}$ alkylsulfinylalkyl, $C_{1-6}$ alkylsulfonylalkyl, or $C_{2-6}$ alkynyl and $R_6$ is optionally substituted with halogen, —OH, alkyloxy, —CN, —COO-lower alkyl, —CONH-lower alkyl, —CON(lower alkyl)$_2$, dialkylamino, phenyl, or heterocyclyl, or a pharmaceutically acceptable derivative thereof.

17 Claims, No Drawings

SUBSTITUTED 1-(4-AMINOPHENYL) IMIDAZOLES AND THEIR USE AS ANTI-INFLAMMATORY AGENTS

BACKGROUND OF THE INVENTION

It has been well established that T-cells play an important role in regulating immune response (F. Powrie and R. L. Coffman, Immunol. Today, 1993, 14, 270). Indeed, activation of T-cells is often the initiating event in many inflammatory and autoimmune diseases. IL-2 is an autocrine growth factor which plays an essential role in the regulation of T-cell activation and proliferation. Clinical studies have shown that interference with IL-2 activity effectively suppresses immune response in vivo (T. A. Waldmann, Immunol. Today, 1993, 14, 264). Accordingly, agents which inhibit IL-2 production are therapeutically useful for selectively suppressing immune response in a patient in need of such immunosuppression.

Previously, others have attempted to interfere with the activity of IL-2 by using cytokine antagonists, monoclonal antibodies, toxins and other biologics which seek to prevent IL-2 from binding to its receptor (G. Mazur and I. Frydecka, Acta Haematol. Pol., 1993, 24, 307). More recently, others have attempted to inhibit IL-2 production at the T-cell level, for example by blocking the expression of IL-2 mRNA with glucocorticoids or cyclosporin A. However, to date, the reported compounds suffer from several disadvantages such as low potency, poor in vivo activity, toxicity and poor oral bioavailability. Accordingly, a need exists for compounds that can effectively inhibit IL-2 production for preventing and treating immune disorders.

U.S. application Ser. No. 09/324,933 discloses substituted 1-(4-aminophenyl)pyrazoles as anti-inflammatory agents. WO9919303 describes substituted phenyl-, heteroaryl- and heterocyclyl-substituted pyrazoles as useful in the treatment of allergy, inflammatory and autoimmune diseases. WO9951580 describes substituted pyrazoles as inhibitors of cytokine production.

BRIEF SUMMARY OF THE INVENTION

The compounds of this invention are 1-(4-aminophenyl) imidazoles optionally substituted on the imidazole ring and on the amino group on the 4-position of the phenyl ring, having antiinflammatory activity by virtue of their ability to inhibit IL-2 production in T-lymphocytes.

In its broadest generic aspect, the invention comprises 1-(4-aminophenyl)imidazoles of Formulas Ia and Ib

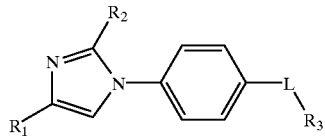
Formula Ia

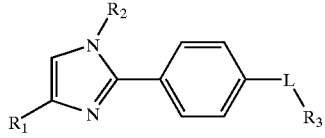
Formula Ib wherein:

$R_1$ and $R_2$, which may be the same or different, are $CF_3$; halogen; CN; branched or unbranched $C_{1-8}$ alkyl; branched or unbranched $C_{1-8}$ alkenyl; $C_{3-8}$ cycloalkyl optionally substituted with OH, CN or methoxy; $C_{1-8}$ alkoxy; $C_{1-4}$ alkyloxyalkyl; $C_{1-8}$ alkylthio; $C_{1-4}$ alkylthioalkyl; $C_{1-8}$ dialkylamino; $C_{1-4}$ dialkylaminoalkyl; $CO_2R_4$ where $R_4$ is $C_{1-4}$ alkyl or $C_{1-4}$ alkenyl optionally substituted with carbocyclyl or heterocyclyl; aryl or heterocyclyl connected to the imidazole in any position that makes a stable bond which aryl or heterocyclyl may be optionally substituted with halogen, $C_{1-4}$ alkyl, $C_{1-4}$ alkenyl, CN, $Me_2N$, $CO_2Me$, OMe, aryl, heterocyclyl or $R_4$;

L is —NHC(O)—; —NHC(O)O—; —NHC(O)C(O)—; —NHC(S)—; —NH—; —NHC(O)NH—; —NHC(S)NH—; —NHCH—$_2$; —NHCH($R_5$)— where $R_5$ is H, CN, $C_{1-6}$ alkyl, $C_{1-6}$ alkyloxyoalkyl $C_{1-6}$ alkythioalkyl, $C_{1-6}$ alkylsulfinylalkyl, $C_{1-6}$ alkysulfonylalkyl, $C_{3-6}$ cycloalkyl, heterocyclyl or aryl optionally substituted with a halogen, $C_{1-4}$ alkyl, CN, $Me_2N$, $CO_2Me$ or OMe; or L is —NHC($R_5$)-lower alkyl;

$R_3$ is $C_{1-8}$ alkyl; $C_{1-8}$ alkyloxy; $C_{1-8}$ alkylthio; $C_{1-8}$ alkylamino; $C_{1-4}$ alkoxyalkyl; $C_{1-4}$ alkylthioalkyl; $C_{1-4}$ alkylaminoalkyl; $C_{1-4}$ dialkylalkylaminoalkyl; carbocyclyl or heterocyclyl, which carbocyclyl or heterocyclyl may optionally be substituted with one or more of the following: halogen, —CN, —$NO_2$, —$SO_2NH_2$ or $R_6$ (where $R_6$ is phenyl, heterocyclyl, $C_{3-6}$-cycloalkyl, $C_{1-6}$-alkyl, $C_{2-6}$-alkenyl, $C_{1-6}$-alkyloxyalkyl, $C_{1-6}$-alkylthioalkyl, $C_{1-6}$-alkylsulfinylalkyl, $C_{1-6}$-alkylsulfonylalkyl or $C_{2-6}$-alkynyl) and $R_6$ may be optionally substituted with halogen, —OH, alkyloxy, —CN, —COO-lower alkyl, —CONH-lower alkyl, —CON (lower alkyl)$_2$, dialkylamino, phenyl or heterocylcyl; or $R_3$ is —$CO_2R_6$; —$N(R_2)$; —$NH(R_6)$; —$C(O)R_6$; —$OR_6$; $S(O)_nR_6$ where n is 0, 1 or 2; —$SO_2NHR_6$; or —$SO_2N(R_6)_2$; or a pharmaceutically acceptable derivative thereof.

DETAILED DESCRIPTION OF THE INVENTION

In order that the invention herein described may be more fully understood, the following detailed description is set forth. As used herein, the following abbreviations are used:

DMAP is 4-dimethylamino pyridine;
DMF is dimethylformamide;
DMSO is dimethylsulfoxide;
Et is ethyl;
EtOAc is ethyl acetate;
Me is methyl;
MeOH is methanol; and
EDC is 1-(3-dimethylaminopropyl)-3-ethylcarbodiimide hydrochloride.

Also, as used herein, each of the following terms, used alone or in conjunction with other terms, are defined as follows (except where noted to the contrary):

The term "alkyl" refers to a saturated aliphatic radical containing from one to ten carbon atoms. "Alkyl" refers to both branched and unbranched alkyl groups. Preferred alkyl groups are straight chain alkyl groups containing from one to eight carbon atoms and branched alkyl groups containing from three to eight carbon atoms. More preferred alkyl groups are straight chain alkyl groups containing from one to six carbon atoms and branched alkyl groups containing from three to six carbon atoms. "Alkyl", as used herein, includes unsubstituted alkyl radicals, those radicals that are partially or fully halogenated and those radicals substituted with one to four, preferably one or two, substituents selected from amino, cyano, nitro, methoxy, ethoxy and hydroxy. The term "cycloalkyl" refers to the cyclic analog of an alkyl group, as defined above. Preferred cycloalkyl groups are saturated cycloalkyl groups containing from three to eight carbon atoms, and more preferably three to six carbon atoms. "Alkyl" and "cycloalkyl", as used herein, include unsubstituted alkyl and cycloalkyl radicals, those radicals that are partially or fully halogenated and those radicals substituted with one to four, preferably one or two, substituents selected from halo, amino, cyano, nitro, methoxy, ethoxy and hydroxy. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom.

The terms "alkenyl" and "alkynyl" refer to a mono- or polyunsaturated aliphatic hydrocarbon radical containing from two to twelve carbon atoms, containing at least one double or triple bond, respectively. "Alkenyl" and "alkynyl" refer to both branched and unbranched alkenyl and alkynyl groups. Preferred alkenyl and alkynyl groups are straight chain alkenyl or alkynyl groups containing from two to eight carbon atoms and branched alkenyl or alkynyl groups containing from five to ten carbon atoms. More preferred alkenyl and alkynyl groups are straight chain alkenyl or alkynyl groups containing from two to six carbon atoms and branched alkenyl or alkynyl groups containing from five to eight carbon atoms. "Alkenyl" and "alkynyl", as used herein, include unsubstituted alkenyl or alkynyl radicals, those radicals that are partially or fully halogenated and those radicals substituted with one to four, preferably one or two, substituents selected from halo, amino, cyano, nitro, methoxy, ethoxy and hydroxy.

The term "aryl" refers to phenyl and naphthyl, phenyl and naphthyl that are partially or fully halogenated and phenyl and naphthyl substituted with halo, alkyl, hydroxy, nitro, —COOH, —CO(lower alkoxy), —CO(lower alkyl), amino, alkylamino, dialkylamino, alkoxy, —NCOH, —NCO(lower alkyl), —NSO$_2$-Ph(halo)$_{0-3}$, Ph, —O-Ph; naphthyl, —O-naphthyl, pyrrolyl, pyrrolyl substituted with lower alkyl, pyridyl, pyridinyl, pyrazinyl, pyrimidinyl and pyridazinyl.

The term "halo" refers to a halogen radical selected from fluoro, chloro, bromo or iodo. Preferred halo groups are fluoro, chloro and bromo.

The term "carbocyclyl" refers to a stable 3–8 membered (but preferably, 5 or 6 membered) monocyclic or 7–11 membered bicyclic radical which may be either saturated or unsaturated, aromatic or non-aromatic. Preferred carbocycles include, for example, phenyl, naphthyl, cyclopropyl, cyclobutyl, cyclopentyl, cyclohexyl, cycloheptyl, cyclopentenyl, cyclohexenyl, cycloheptenyl, indanyl, indenyl, dihydronaphthyl and tetrahydronaphthyl. Most preferred heterocycles of this invention are phenyl, naphthyl, cyclohexyl, tetrahydronaphthyl and indanyl. "Carbocyclyl" refers to unsubstituted carbocyclic radicals, those radicals that are partially or fully halogenated and those radicals substituted with alkyl; hydroxyl; nitro; —COOH; —CO(lower alkoxy); —CO(lower alkyl); amino; alkylamino; dialkylamino; alkoxy; —NCHO; —NCO(lower alkyl); —NSO$_2$-Ph(halo)$_{0-3}$; Ph; —O-Ph; naphthyl; —O-naphthyl; pyrrolyl; pyrrolyl substituted with lower alkyl; pyridyl; pyridinyl; pyrazinyl; pyrimidinyl and pyridazinyl.

The term "heterocycle" refers to a stable 5–8 membered (but preferably, 5 or 6 membered) monocyclic or 8–11 membered bicyclic heterocycle radical which may be either saturated or unsaturated, aromatic or non-aromatic, and which may be optionally benzo- or pyridofused if monocyclic. Each heterocycle consists of carbon atoms and from 1 to 4 heteroatoms selected from the group consisting of nitrogen, oxygen and sulfur. As used herein, "nitrogen" and "sulfur" include any oxidized form of nitrogen and sulfur and the quaternized form of any basic nitrogen. The heterocycle may be attached by any atom of the cycle, which results in the creation of a stable structure. Preferred heterocycles include, for example, benzimidazolyl, furyl, imidazolyl, imidazolinyl, imidazolidinyl, quinolinyl, isoquinolinyl, indolyl, oxazolyl, pyridyl, pyrrolyl, pyrrolinyl, pyrazolyl, pyrazinyl, pyrimidinyl, pyridazinyl, quinoxolyl, piperidinyl, morpholinyl, thiomorpholinyl, furyl, thienyl, triazolyl, thiazolyl, β-carbolinyl, tetrazolyl, thiazolidinyl, benzofuranoyl, thiomorpholinyl sulfone, benzoxazolyl, oxopiperidinyl, oxopyrrolidinyl, oxoazepinyl, azepinyl, isoxazolyl, tetrahydropyranyl, tetrahydrofuranyl, thiadiazoyl, benzodioxolyl, tetrahydrothiophenyl and sulfolanyl. Most preferred heterocycles of this invention include imidazolyl, pyridyl, pyrrolyl, pyrazolyl, piperidinyl, morpholinyl, furyl, thienyl, thiazolyl and the benzo- and pyrido-fused derivatives thereof. "Heterocyclyl" refers to unsubstituted heterocycle radicals, those radicals that are partially or fully halogenated and those radicals substituted with alkyl, hydroxyl, nitro, —COOH, —CO(lower alkoxy), —CO(lower alkyl), amino, alkylamino, dialkylamino, alkoxy, —NCHO, —NCO(lower alkyl), —NSO$_2$-Ph(halo)$_{0-3}$, Ph, —O-Ph, naphthyl, —O-naphthyl, pyrrolyl, pyrrolyl substituted with lower alkyl, pyridyl, pyridinyl, pyrazinyl, pyrimidinyl and pyridazinyl.

The term "lower" used in conjunction with other terms (e.g., "alkyl", "alkoxy" and the like) refers to a radical containing from one to six, preferably from one to five and more preferably, from one to four carbon atoms. For example, a "lower alkyl" group is a branched or unbranched alkyl radical containing from one to six carbon atoms.

The term "patient" refers to a warm-blooded animal, and preferably a human.

The term "pharmaceutically acceptable carrier" or "pharmaceutically acceptable adjuvant" refers to a non-toxic carrier or adjuvant that may be administered to a patient together with a compound of this invention and which does not destroy the pharmacological activity of that compound.

It should be understood that any compounds of this invention containing one or more asymmetric carbon atoms may occur as racemates and racemic mixtures, single enantiomers, diastereomeric mixtures and individual diastereomers. All such isomeric forms of these compounds are expressly included in the present invention. Each stereogenic center may be in the R or S configuration, or a combination of configurations.

The compounds of this invention are defined to include pharmaceutically acceptable derivatives thereof. A "pharmaceutically acceptable derivative" refers to any pharmaceutically acceptable salt, ester, or salt of an ester of a compound of this invention, or any other compound which, upon administration to a patient, is capable of providing (directly or indirectly) a compound of this invention, a pharmacologically active metabolite or pharmacologically active residue thereof.

Combinations of substituents and variables encompassed by this invention are only those that result in the formation of stable compounds. The term "stable" as used herein, refers to compounds which possess stability sufficient to permit manufacture and administration to a patient by conventional methods known in the art. Typically, such compounds are stable at a temperature of 40° C. or less, in the absence of moisture or other chemically reactive conditions, for at least a week.

The compounds of this invention may be used in the form of salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pectinate, persulfate, 3-phenylpropionate, picrate, pivalate, propionate, succinate, tartrate, tosylate and undecanoate.

This invention relates to substituted 1-(4-aminophenyl) imidazoles and analogs thereof that inhibit interleukin-2 (IL-2) production. In one embodiment, this invention relates to a novel class of substituted 1-(4-aminophenyl)imidazoles and pharmaceutical compositions comprising these compounds. Because of their selective immunomodulating properties, the compounds and pharmaceutical compositions of this invention are particularly well suited for preventing and treating immune disorders, including autoimmune disease, inflammatory disease, organ transplant rejection and other disorders associated with IL-2 mediated immune response.

The substituted 1-(4-aminophenyl)imidazoles of this invention are represented by Formulas Ia and Ib

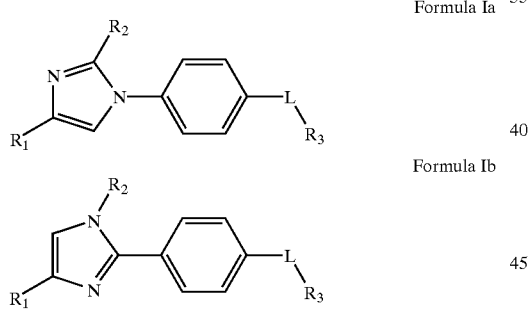

Formula Ia

Formula Ib wherein:
$R_1$ and $R_2$, which may be the same or different, are $CF_3$; halogen; CN; branched or unbranched $C_{1-8}$ alkyl; branched or unbranched $C_{1-8}$ alkenyl; $C_{3-8}$ cycloalkyl optionally substituted with OH, CN or methoxy; $C_{1-8}$ alkoxy; $C_{1-4}$ alkyloxyalkyl; $C_{1-8}$ alkylthio; $C_{1-4}$ alkylthioalkyl; $C_{1-8}$ dialkylamino; $C_{1-4}$ dialkylaminoalkyl; $CO_2R_4$ where $R_4$ is $C_{1-4}$ alkyl or $C_{1-4}$ alkenyl optionally substituted with carbocyclyl or heterocyclyl; aryl or heterocyclyl connected to the imidazole in any position that makes a stable bond which aryl or heterocyclyl may be optionally substituted with halogen, $C_{1-4}$ alkyl, $C_{1-4}$ alkenyl, CN, $Me_2N$, $CO_2Me$, OMe, aryl, heterocyclyl or $R_4$;

L is —NHC(O)—; —NHC(O)O—; —NHC(O)C(O)—; —NHC(S)—; —NH—; —NHC(O)NH—; —NHC(S)NH—; —NHCH—$_2$; —NHCH($R_5$)— where $R_5$ is H, CN, $C_{1-6}$ alkyl, $C_{1-6}$ alkyloxyalkyl $C_{1-6}$ alkythioalkyl, $C_{1-6}$ alkylsulfinylalkyl, $C_{1-6}$ alkysulfonylalkyl, $C_{3-6}$ cycloalkyl, heterocyclyl or aryl optionally substituted with a halogen, $C_{1-4}$ alkyl, CN, $Me_2N$, $CO_2Me$ or OMe; or L is —NHC($R_5$)-lower alkyl;

$R_3$ is $C_{1-8}$ alkyl; $C_{1-8}$ alkyloxy; $C_{1-8}$ alkylthio; $C_{1-8}$ alkylamino; $C_{1-4}$ alkoxyalkyl; $C_{1-4}$ alkylthioalkyl; $C_{1-4}$ alkylaminoalkyl $C_{1-4}$ dialkylalkylaminoalkyl; carbocyclyl or heterocyclyl, which carbocyclyl or heterocyclyl may optionally be substituted with one or more of the following:

halogen, —CN, —$NO_2$, —$SO_2NH_2$ or $R_6$ (where $R_6$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-6}$ alkylthioalkyl, $C_{1-6}$ alkylsulfinylalkyl, $C_{1-6}$ alkylsulfonylalkyl or $C_{2-6}$ alkynyl) and $R_6$ may be optionally substituted with halogen, —OH, alkyloxy, —CN, —COO-lower alkyl, —CONH-lower alkyl, —CON(lower alkyl)$_2$, dialkylamino, phenyl or heterocylcyl; or $R_3$ is —$CO_2R_6$; —$N(R_6)2$; —$NH(R_6)$; —$C(O)R_6$; —$OR_6$; $S(O)_nR_6$ where n is O, 1 or 2; —$SO_2NHR_6$; or —$SO_2N(R_6)_2$; or a pharmaceutically acceptable derivative thereof.

Preferably, the novel substituted 1-(4-aminophenyl) imidazoles of Formula Ia or Ib are those wherein:
$R_1$ is straight-chained, branched or cyclo-$C_{3-8}$alkyl, alkenyl, or alkynyl; $C_{1-3}$alkyloxyalkyl, $C_{1-5}$ alkyloxy, $C_{1-3}$alkylthioalkyl, $C_{1-5}$alkylthio, $CF_3$; heterocyclyl or aryl optionally substituted with halogen, $C_{1-4}$alkyl, CN, alkoxy or $Me_2N$;

$R_2$ is halogen, Me, Et, $CF_3$, CN, cyclopropyl, vinyl, SMe, OMe, heterocyclyl or aryl optionally substituted with halogen, $C_{1-4}$ alkyl, CN, alkoxy or $Me_2N$;

L is —NHC(O)—, —NH—, —NHC(O)NH, or —NHCH ($R_5$)—, where $R_5$ is H, $C_{1-4}$ alkyl, or CN and $R_3$ is $C_{1-6}$ alkyl, $C_{1-4}$ alkyloxyalkyl, $C_{1-4}$ alkylthioalkyl, cyclohexyl, cyclopentyl, indanyl, indolyl, phenyl, thienyl, naphthyl, isoxazolyl or pyridyl, optionally substituted with one or more halogen, —CN, —$NO_2$, $SO_2NH_2$, or $R_6$ where $R_6$ is $C_{1-6}$ alkyl, $C_{2-6}$ alkenyl, $C_{1-6}$ alkyloxyalkyl, $C_{1-6}$ alkylthioalkyl, or $C_{2-6}$ alkynyl, optionally substituted with OH, CN, —COO-lower alkyl, —CONH-lower alkyl, —CON(lower alkyl)$_2$, dialkylamino, or heterocycyl, $CO_2R_6$, —$N(R_6)_2$, —NH ($R_6$), —$C(O)R_6$, —$OR_6$, $S(O)_nR_6$ where n is 0, 1 or 2, —$SO_2NHR_6$, —$SO_2N(R_6)_2$.

More preferred are novel substituted 1-(4-aminophenyl) imidazoles of Formula Ia or Ib wherein:
$R_1$ is Et, i-Pr, n-Pr, t-Bu, cyclopentyl, $CF_3$, —OEt, $MeOCH_2$—, 2- or 3-tetrahydrofuranyl, 2-, 3-, or 4-pyridyl, 2-furanyl, or 2-thiazolyl;

$R_2$ is CN, $CF_3$, Cl, Me, Et, SMe, cyclopropyl, vinyl, or 2-furanyl;

L is —NHC(O)—, —NH— or —NHCH$_2$—; and $R_3$ is a phenyl ring which is optionally substituted with one to three groups selected from $C_{1-3}$alkyl, chloro, fluoro, $CF_3$, $OC_{1-4}$alkyl, $OC_{3-5}$alkenyl, $CO_2C_{1-2}$alkyl, SMe, CN, $NO_2$, $NMe_2$ and $O(CH_2)_pR_7$, where p is 3 or 4 and $R_7$ is CN, $CO_2Me$, 2-(1,3-dioxolanyl), OH, or $OC_6H_5$; 1- or 2-indanyl, 2-tetrahydropyranyl, or a heterocycle selected from the group consisting of 2-thienyl, 3-furanyl, 3- or 4-pyridyl, 4-isoxazolyl, 1-isoquinolinyl, 2-indolyl, 2-benzothienyl and 4-pyrazolyl, which may be optionally substituted with one to three groups selected from Cl, Br, Me, CN, $CF_3$, $OCF_3$, $NO_2$, or $O(CH_2)_pR_7$, where p is 3 or 4 and $R_7$ is CN, $CO_2Me$, 2-(1,3-dioxolanyl), OH, or $OC_6H_5$; $C_{5-6}$ alkyl, $C_{5-6}$cycloalkyl, or cyclohexenyl.

Especially preferred are novel substituted 1-(4-aminophenyl)imidazoles of Formula Ia or Ib wherein:

$R_1$ is i-Pr, $CF_3$, 3-pyridyl or 4-pyridyl;

$R_2$ is CN, $CF_3$, Cl, Me, SMe or Et;

L is —NHC(O)—, —NH— or —NHCH$_2$—; and $R_3$ is a phenyl ring which is optionally substituted with $O(CH_2)_3R_8$, where $R_8$ is CN, OH or 2-(1,3-dioxolanyl); $OC_{3-4}$alkyl, $O(CH_2)_4OH$, 1-pentenyl, one to three groups selected from Me, Cl, F and CN; 3-pyridyl optionally substituted in the 6-position with $O(CH_2)_2OEt$ or $O(CH_2)_3R_8$, where $R_8$ is CN, OH or 2-(1,3-dioxolanyl); 4-pyridinyl optionally substituted with a chlorine, 2-thienyl optionally substituted with Me or Br, 3,5-dimethyl-4-isoxazolyl, 1-methyl-2-indolyl, cyclopentyl, cyclohexyl, 1-indanyl or n-pent-3-yl.

Compounds of Formula Ia or Ib in which L is —NHC(O)— may be prepared by one of the methods outlined below. For example, a (4-aminophenyl) disubstituted imidazole 1a or 1b may be reacted with a carboxylic acid 2 under suitable coupling conditions known to one skilled in the art, for example in the presence of EDC and a base catalyst such as N,N-dimethylaminopyridine in a suitable solvent such as methylene chloride acetonitrile or DMF (Method A). Alternatively, 1a or 1b could be coupled with an acid halide 3 in the presence of a suitable base such as triethylamine in a suitable solvent such as methylene chloride (Method B).

Method A

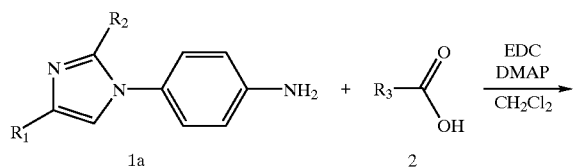

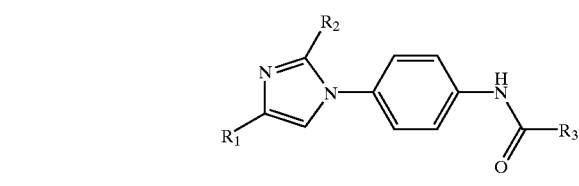

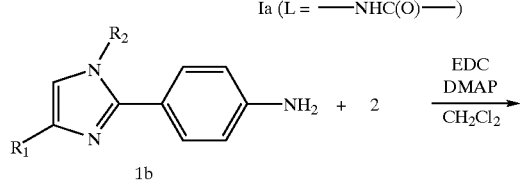

Method B

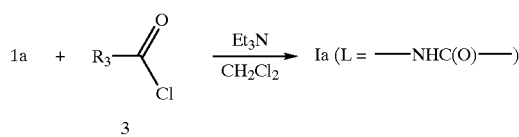

-continued

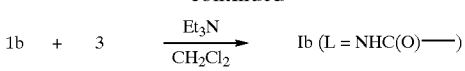

Compounds of Formula Ia or Ib in which L is —NH— and $R_3$ is a heteroaryl ring may be prepared, as illustrated below, by reaction of 1a or 1b with a heterocycle 4 containing a labile substituent such as a halogen, which may be displaced by nucleophilic substitution (Method C). The reaction may be carried out in a sealed tube or an open vessel, at ambient temperature or heated to 150° C. in a suitable solvent such as dioxane or THF. A base such as sodium bis-trimethylsilyl amide may be added to the reaction.

Method C

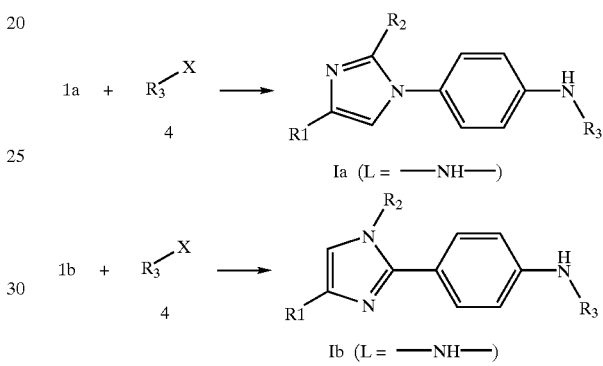

X is halogen or other leaving group

Compounds in which L is —NHC(O)NH— may be prepared by reaction of isocyanate 5a or 5b with an amine 6 in a suitable solvent such as methylene chloride or toluene (Method D). An amine such as triethylamine may be added. Alternatively, 1a or 1b could be reacted with an amine carbonyl chloride such as N-morpholine carbonyl chloride 7 in a suitable solvent such as methylene chloride (Method E). Intermediates 5a and 5b may be prepared from 1a and 1b, respectively, by methods known to those skilled in the art, for example by reaction of 1a or 1b with phosgene or a phosgene equivalent in the presence of a suitable base such as potassium carbonate, in a suitable solvent, such as methylene chloride.

Method D

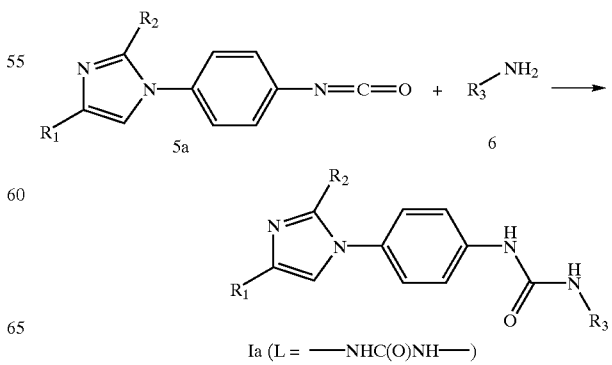

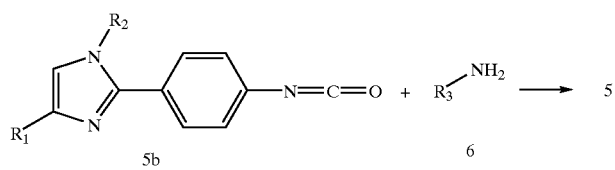

5b + 6 → 5

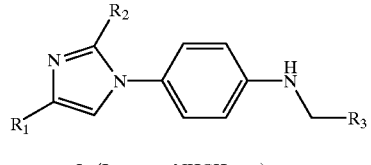

Method G

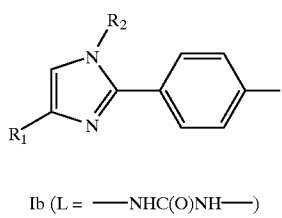

Ib (L = —NHC(O)NH—)

Method E

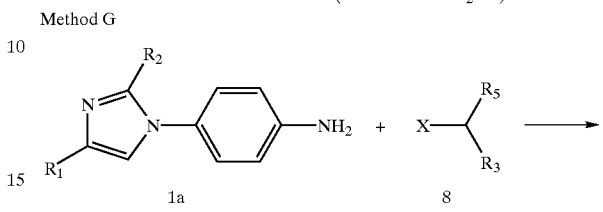

Ia (L = —NHCH($R_5$)—)

1a + 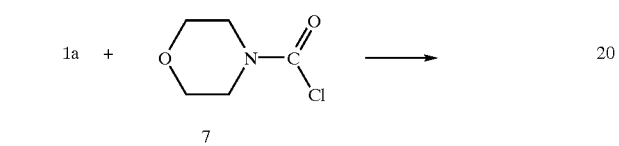 →

7

Methods H and I

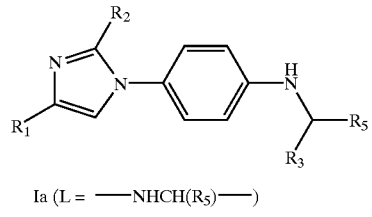

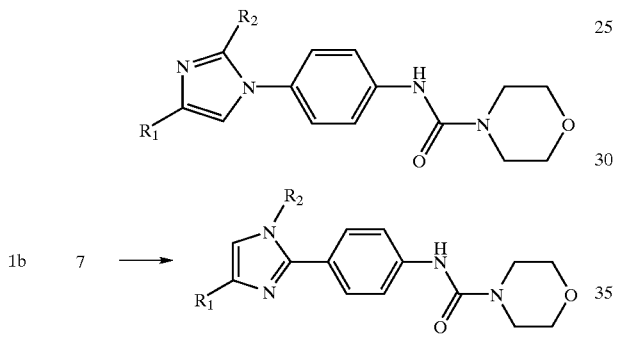

1b + 7 →

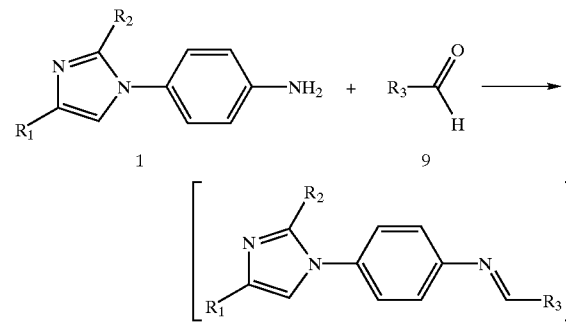

Methods by which compounds in which L is —NHCH($R_5$)— or —NHCH$_2$ may be prepared are illustrated below. The procedures are illustrated for Ia, but may be used for Ib as well by substituting the appropriate starting material. For example, these compounds may be prepared by reduction of the corresponding amide (Ia or Ib, L is —NHC(O)—) with a suitable reducing agent such as lithium aluminum hydride, in a suitable solvent such as THF or diethyl ether (Method F). Alternatively, amine 1a or 1b could react with an alkylating agent 8 (Method G) where X is a suitable leaving group such as a halogen. In another alternate procedure, amine 1a or 1b could react with an aldehyde 9, and the intermediate imine 10 reacted with a reducing agent such as sodium cyanoborohydride or sodium triacetoxyborohydride (Method I). Alternatively, 10 could be reacted with a nucleophile such as an alkyl or aryl lithium reagent (Method I).

Method F

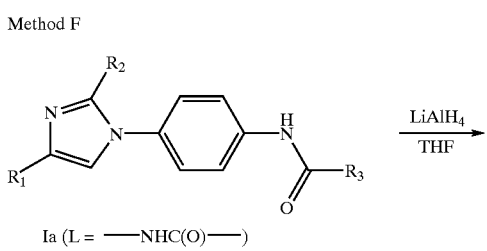

Ia (L = —NHC(O)—)

Intermediates useful in the synthesis of compounds of formula Ia may be prepared as described below. A 3,5-disubstituted imidazole may be reacted with nitrobenzene substituted in the 4-position with a leaving group such as a halogen in the presence of a base (Method J). The nitrophenylimidazoles (11) produced could then be reduced to aminophenyl imidazoles by using a reducing agent such as SnCl$_2$ or hydrogen or a hydrogen source such as ammonium formate in the presence of a catalyst such as palladium. Desired 3,5-disubstituted imidazoles may be prepared by methods known to those skilled in the art, such as by reaction of an alpha-bromoketone ($R_1C(O)CH_2Br$) with an amidine ($R_2C(=NH)NH_2$) (for example, see T. L. Little and S. E. Webber, J. Org Chem., 1994, 59, 7299).

Method J

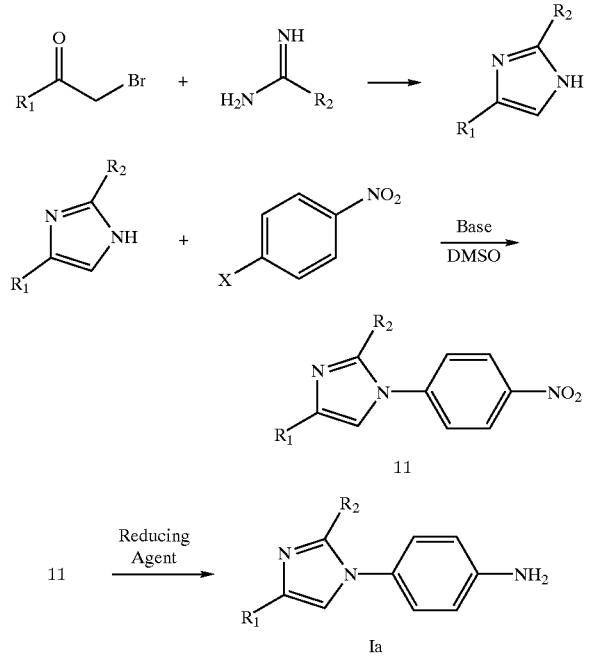

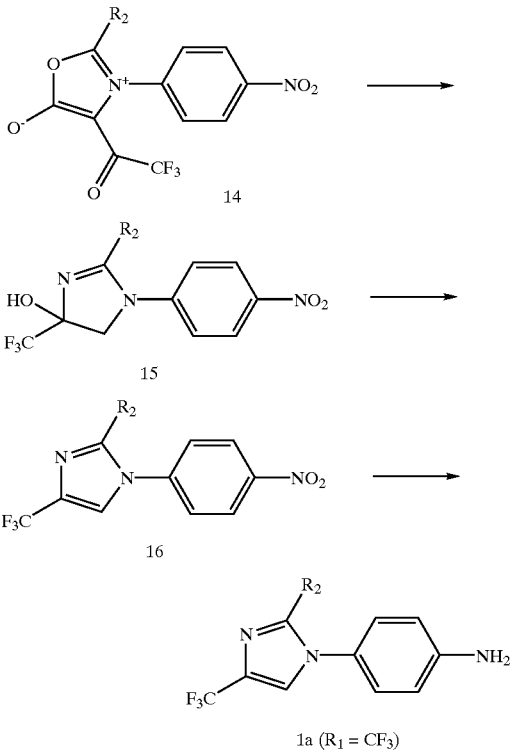

Intermediates 1a, in which $R_1$ is $CF_3$, useful in several of the Methods described above, may be prepared using a general procedure described in the chemical literature (M. Kawase et al., Heterocycles, 1995, 41, 1617) and illustrated by Method K below.

Method K

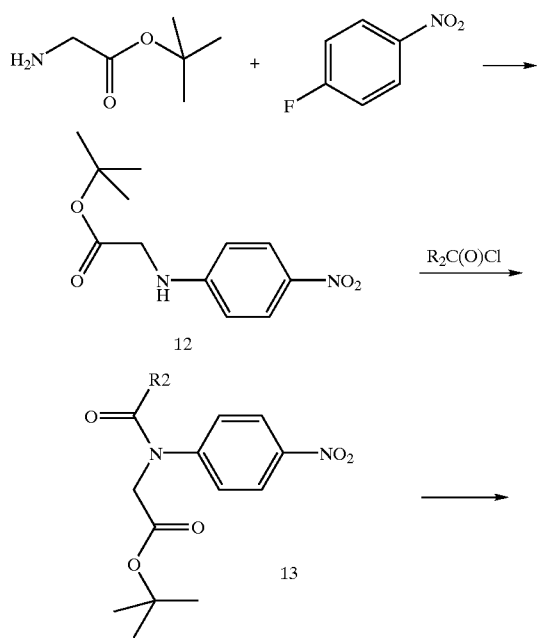

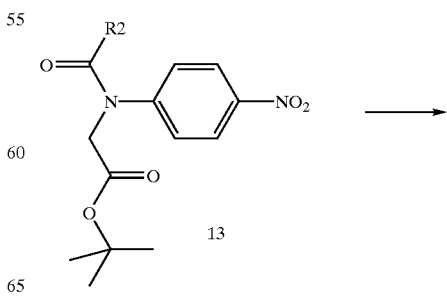

In this procedure, a protected glycine, such as glycine t-butyl ester, is reacted with a 4-halonitrobenzene, such as 4-fluoronitrobenzene, in the presence of a suitable base, such as potassium carbonate, to provide 12, This is acylated with an acyl chloride $R_2C(O)Cl$, to provide 13. Removal of the t-butyl ester by reaction with a suitable acid such as trifluoroacetic acid, is followed treatment with trifluoroacetic anhydride resulting in cyclization to mesoionic species 14. Treatment with ammonium acetate provides 15, which under suitable dehydration conditions, for example treatment with $POCl_3$ in pyridine, provides imidazole 16. This may then be reduced as described above (Method J) to the desired 1a ($R_1=CF_3$).

Method K may be adapted to prepare compounds of the invention with other $R_1$. By substituting an acid chloride ($R_1C(O)Cl$) or acid anhydride ($R_1C(O)OC(O)R_1$) and a suitable base, such as dimethylaminopyridine, for trifluoroacetic anhydride in the conversion of 13 to 14 above, one may obtain 14a with the desired $R_1$. This may then be converted to the desired 1a as described in Method K.

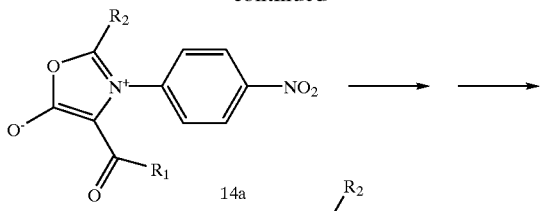

By altering the positions of the substituents, Method K may be modified to produce compounds of formula Ib as illustrated by Method K'. In this procedure, an N-substituted glycine ester, such as the methyl ester shown below is reacted with 4-nitrobenzoyl chloride in a suitable solvent such as methylene chloride or THF, in the presence of a suitable base, such as triethylamine or N-methylmorpholine to provide 17. Hydrolysis, followed by treatment with an acid chloride or acid anhydride, in a fashion analogous to the conversion of 13 to 14a, provides 18. This is then converted to the desired intermediate 1b as described for the conversion of 14 to 1a in Method K.

Method K'

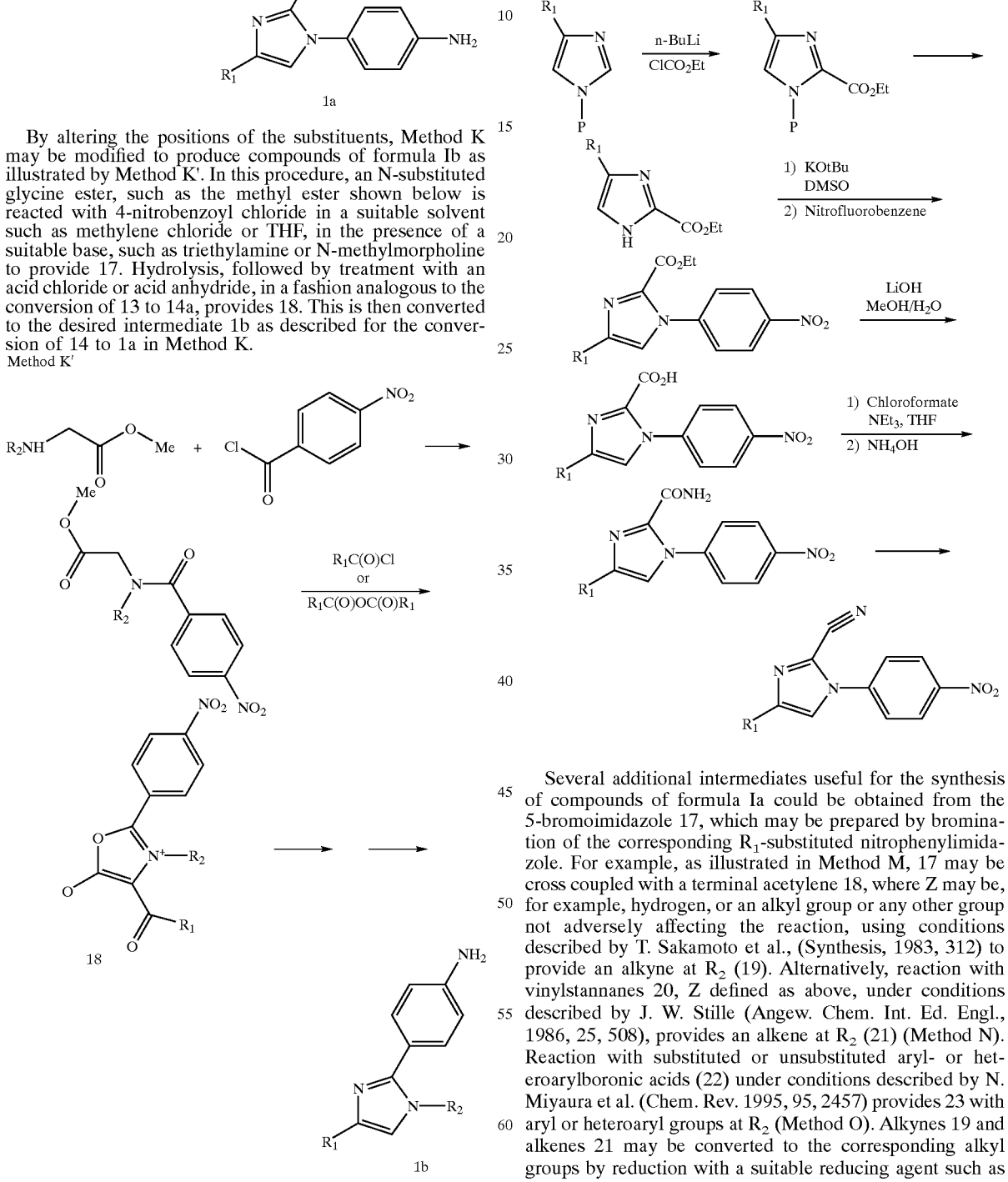

Method L illustrates another procedure by which 2-cyanoimidazoles may be obtained. A suitably protected substituted imidazole, where the protecting group P is trityl for example, may be reacted with a strong base, such as n-butyl lithium, and the resulting anion reacted with ethyl chloroformate to give the ethyl ester. Deprotection may be followed by reaction with nitrofluorobenzene (Method J) to give the nitrophenyl imidazole ester. The ester may then be converted to the nitrile by methods known to those skilled in the art, for example by conversion to the amide and dehydration as illustrated below.

Method L

Several additional intermediates useful for the synthesis of compounds of formula Ia could be obtained from the 5-bromoimidazole 17, which may be prepared by bromination of the corresponding $R_1$-substituted nitrophenylimidazole. For example, as illustrated in Method M, 17 may be cross coupled with a terminal acetylene 18, where Z may be, for example, hydrogen, or an alkyl group or any other group not adversely affecting the reaction, using conditions described by T. Sakamoto et al., (Synthesis, 1983, 312) to provide an alkyne at $R_2$ (19). Alternatively, reaction with vinylstannanes 20, Z defined as above, under conditions described by J. W. Stille (Angew. Chem. Int. Ed. Engl., 1986, 25, 508), provides an alkene at $R_2$ (21) (Method N). Reaction with substituted or unsubstituted aryl- or heteroarylboronic acids (22) under conditions described by N. Miyaura et al. (Chem. Rev. 1995, 95, 2457) provides 23 with aryl or heteroaryl groups at $R_2$ (Method O). Alkynes 19 and alkenes 21 may be converted to the corresponding alkyl groups by reduction with a suitable reducing agent such as hydrogen in the presence of a suitable catalyst such as platinum or palladium to provide 1a (see Method J), with an alkyl group at $R_2$. Alternatively, reaction with a reducing agent that leaves alkenes and alkynes intact, such as $SnCl_2$ provides 1a with alkenes or alkynes at $R_2$.

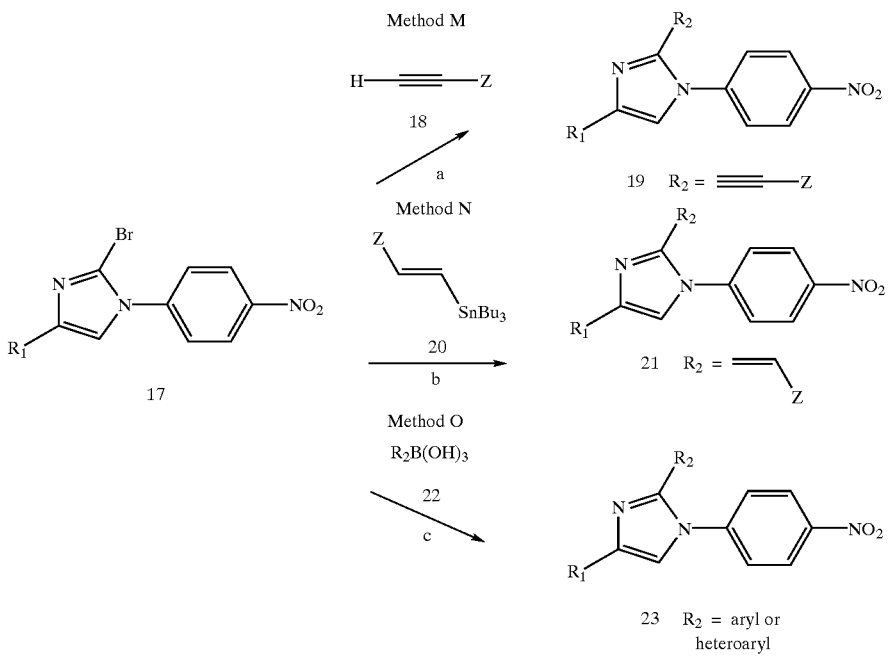

a. Pd(PPh₃)₄, CuBrSMe₂, Et₃N
b. Pd(PPh₃)₄, THF
c. Pd(PPh₃)₄, 2M Na₂CO₃, THF

Method P describes an alternate procedure for preparing compounds of Formula Ia or Ib where L is —NH—. As illustrated in below, intermediate 1a may be heated at about 70° C. with an aryl bromide in the presence of a palladium catalyst, preferably Pd₂(dba)₃, 2,2'-bis(diphenylphosphino)-1,1'-binapthyl (BINAP), and a base, preferably NaOt-Bu, in a solvent such as toluene, as described by S. Buchwald et al. (J. Amer. Chem. Soc., 1993, 119, 8451) to provide Ia (L=—NH—). Using the same Method and starting with intermediate 1b would provide Ib (L=—NH—). Alternately, one could employ the same conditions with the bromophenylimidazole 24 and an amine, R₃NH₂, as illustrated for Ia below.

Method P

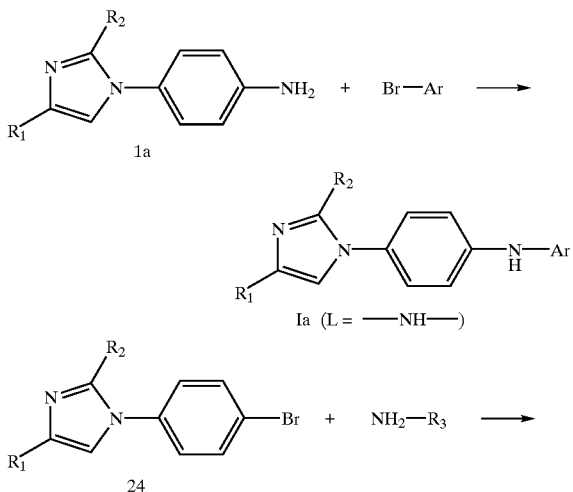

-continued

As can be appreciated by chemists possessing ordinary skill in the art, the synthetic schemes described above are for illustrative purposes only and may be modified using conventional synthetic methodology to produce any of the analogs of Formula I. Depending on precisely how the synthetic schemes are modified, the specific reaction conditions might also require modification. Such modifications may involve the use of higher or lower temperature or pressure, conditions other than those reported herein, or the addition of further synthetic steps such as functional group transformations. However, since progress of the reactions is easily monitored by techniques such as high performance liquid chromatography, gas chromatography, mass spectroscopy, thin layer chromatography, nuclear magnetic resonance spectroscopy and the like, such modifications are well within the skill of the art. Likewise, it should be appreciated that initial products from these Methods could be further modified to make additional compounds of this invention. Intermediates used in the Methods described above may be commercially available or could be prepared from commercially available materials by methods described in the chemical literature and known to people skilled in the art.

The 1-phenylimidazole analogs of Formula Ia and Ib inhibit production of IL-2. Without wishing to be bound by theory, the compounds of this invention inhibit IL-2 production by T-cells. This inhibition of IL-2production is therapeutically useful for selectively suppressing immune function. The result of such selectively suppressed immunity includes reduced cell proliferation of peripheral blood lymphocytes and cellular immune response. Thus, the inhibition of IL-2 production is an attractive means for preventing and treating a variety of immune disorders, including inflammatory diseases, autoimmune diseases, organ and bone marrow transplant rejection and other disorders associated with IL-2 mediated immune response. In particular, the compounds of Formula I may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection) and lupus erythematosus. Other disorders associated with IL-2 mediated immune response will be evident to those of ordinary skill in the art and can also be treated with the compounds and compositions of this invention.

The compounds of this invention may be administered in any conventional dosage form in any conventional manner. Such methods of treatment, including their dosage levels and other requirements, may be selected by those of ordinary skill in the art from available methods and techniques. For example, a compound of this invention may be combined with a pharmaceutically acceptable carrier or adjuvant for administration to a patient in need of such treatment in a pharmaceutically acceptable manner and in an amount effective to treat (including lessening the severity of symptoms) the immune disorder.

The compounds of this invention may be administered alone or in combination with conventional therapeutics, such as conventional immunosuppressants. Advantageously, such combination therapies utilize lower dosages of the conventional therapeutics, thus avoiding possible toxicity and adverse side effects incurred when those agents are used as monotherapies. The compounds of this invention may be physically combined with the conventional therapeutics into a single pharmaceutical composition. Advantageously, the compounds may then be administered together in a single dosage form. Alternatively, the compounds may be administered separately (either serially or in parallel). Separate dosing allows for greater flexibility in the dosing regime.

According to this invention, the compounds of Formula Ia and Ib and the pharmaceutical compositions containing those compounds may be administered to a patient in any conventional manner and in any pharmaceutically acceptable dosage from, including, but not limited to, intravenously, intramuscularly, subcutaneously, intrasynovially, by infusion, sublingually, transdermally, orally, topically or by inhalation. The preferred modes of administration are oral and intravenous.

Dosage forms of the compounds of this invention include pharmaceutically acceptable carriers and adjuvants known to those of ordinary skill in the art. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, Pharmaceutical Dosage Forms and Drug Delivery Systems, 5th ed., Lea and Febiger, 1990). Dosage levels and requirements are well-recognized in the art and may be selected by those of ordinary skill in the art from available methods and techniques suitable for a particular patient.

Typically, dosage levels range from about 10–1000 mg/dose for a 70 kg patient. Although one dose per day may be sufficient, up to 5 doses per day may be given. For oral doses, up to 5000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto and the judgment of the treating physician.

Synthetic Examples

In order that this invention be more fully understood, the following examples are set forth. These examples are for the purpose of illustrating preferred embodiments of this invention, and are not to be construed as limiting the scope of the invention in any way.

EXAMPLE 1

Synthesis of N-[4-(4-methyl-2-phenylimidazol-1-yl)]phenyl]4-chlorobenzamide (Methods J and A)

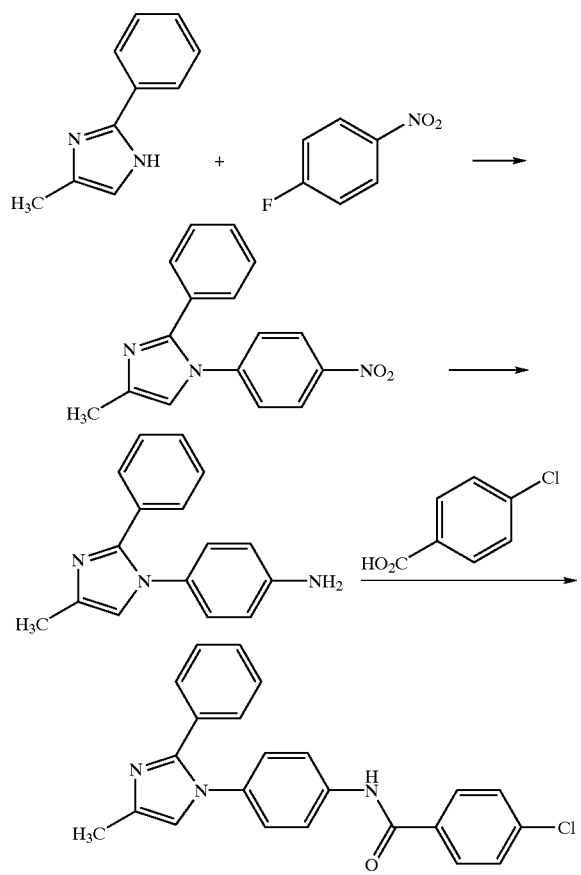

Potassium-t-butoxide (2.24 g, 20 mmol) was added to anhydrous DMSO (16 mL) and stirred at room temperature for 5–10 min until most of the solid dissolved. Then 4-methyl-2-phenylimidazole (3.16 g, 20 mmol) was added and stirring was continued at room temperature for 10 min. 1-Fluoro-4-nitrobenzene (2.12 mL, 20 mmol) was added to the clear solution and the mixture was heated at 90° C. for 1 hr. The reaction mixture was allowed to cool to room temperature and was poured onto crushed ice and extracted with $CH_2Cl_2$ (3×100 mL). The combined extracts were washed with brine, dried over anhydrous $Na_2SO_4$ and concentrated to give a light yellow, thick oil. The yield of crude product was 80%. Proton NMR indicated the product was a single regioisomer.

To a stirred solution of the above nitro compound (6 mmol) in glacial acetic acid (30 mL) was added stannous chloride (8.1 g, 35.9 mmol) in conc. HCl (15 mL). The reaction mixture was stirred at room temperature. TLC after 1 hr showed complete disappearance of the nitro compound. The reaction mixture was cooled in ice, and the pH was brought to 12 by the addition of 10N NaOH. After stirring at room temperature for 15 min, the mixture was diluted with water (50 mL), extracted with $CH_2Cl_2$ (3×50 mL), the combined $CH_2Cl_2$ extracts washed with brine (3×25 mL), dried over anhydrous $Na_2SO_4$ and concentrated to give the desired amine as a reddish orange, thick oil.

4-Chlorobenzoic acid (2 mmol), EDC (2.2 mmol) and DMAP (0.2 mmol) were stirred in $CH_2Cl_2$ (5 mL) and DMF (1mL) for 5 min and then the amine from above (1.5 mmol) was added and the reaction mixture stirred for 16 hr. The solvent was evaporated under vacuum, the residue taken up in water and the precipitated solid filtered off. The crude product was purified by column chromatography over silica gel to give the title compound (m.p. 146–149° C., 70% yield) which was pure by HPLC analysis. $^1$H NMR (DMSO-$d_6$): δ2.21 (3H, s), 7.17 (1H, s), 7.25–7.34 (7H, m), 7.62 (2H, d, J=9 Hz), 7.83 (2H, d, J=9 Hz), 7.98 (2H, d, J=9 Hz), 10.5 (1H, s).

EXAMPLE 2

Synthesis of N-[4-(2-methyl-4-trifluoromethylimidazol-1-yl)]phenyl]4-chlorobenzamide (Methods K and A)

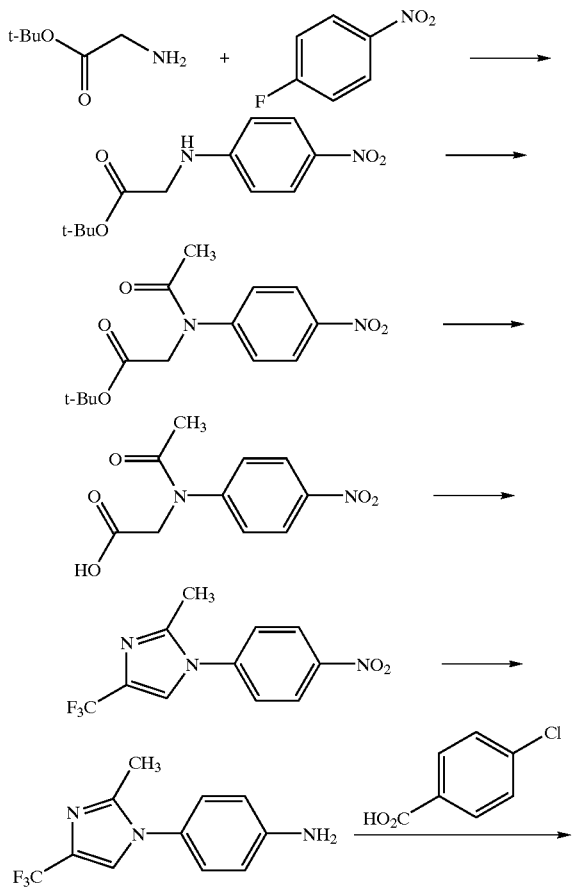

-continued

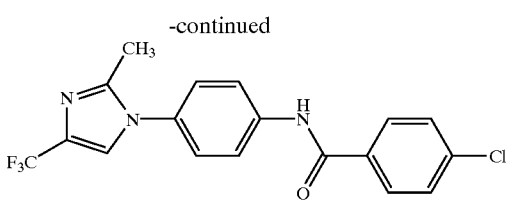

A mixture of glycine tert-butyl ester hydrochloride (3.35 g, 20 mmol), 4-nitrofluorobenzene (2.82 g, 20 mmol) and potassium carbonate (4.2 g, 30 mmol) in DMSO (15 mL) was heated at 90° C. for 22 hr. The reaction mixture was allowed to cool to room temperature and then poured onto crushed ice. The precipitated yellow solid was filtered, washed with water and dried ($Na_2SO_4$) to give N-(4-nitrophenyl)glycine tert-butyl ester (4.1 g, 81%).

To a stirred solution of the above nitro compound (2.77 g, 11 mmol) and N-methylmorpholine (2.6 mL, 24 mmol) in $CH_2Cl_2$ (20 mL) maintained at 0° C. was added acetyl chloride (1.6 mL, 22 mmol)followed by DMAP (122 mg, 1 mmol). The reaction was stirred at room temperature for 24 hr. The solvent was evaporated and the residue treated with ice-cold 1N $H_2SO_4$ (200 mL), extracted with $CH_2Cl_2$ (3×100 mL), the combined extracts washed with ice-cold 1N $H_2SO_4$ (3×50 mL), water (3×50 mL), dried over anhydrous $Na_2SO_4$ and concentrated to give a brownish yellow oil (3.2 g, 100%). Proton NMR indicated it to be the N-acetylated material containing 10% of the starting material. This was used without further purification.

The N-acylated tert-butyl ester (3.2 g) was treated with neat trifluoroacetic acid (50 mL) at room temperature for 1 hr. After evaporation of the trifluoroacetic acid, the residue was taken up in ice-cold water, the resulting yellow precipitate filtered off, washed with water and dried providing the corresponding carboxylic acid (2.4 g).

Trifluoroacetic anhydride (2.12 mL, 15 mmol) was added to a suspension of the above carboxylic acid (1.19 g, 5 mmol) in $CH_2Cl_2$ and stirred at room temperature for 2 hr. The residue obtained after evaporation of excess reagents was triturated with ether to give a reddish yellow solid. This solid was taken up in DMF (20 mL) and ammonium acetate (0.77 g, 10 mmol) was added and the mixture heated at 70° C. for 2 hr. DMF was evaporated under vacuum, the residue was taken up in $CH_2Cl_2$ and cooled on ice. The precipitated solid was filtered and washed with cold $CH_2Cl_2$ to give a light brownish solid (1.1 g, 76%).

A mixture of the above intermediate (0.29 g, 1 mmol), phosphorous oxychloride (223 μL, 2.4 mmol) and pyridine (0.71 mL, 8.8 mmol) was heated at 90° C. for 2 hr. The reaction mixture, after cooling to room temperature, was treated with 10% NaHCO3 (50 mL), extracted with EtOAc (3×50 mL), the combined extracts washed with 10% NaHCO3 (1×50 mL), brine (1×50 mL), dried over anhydrous $Na_2SO_4$ and the solvent evaporated to give a dark brownish, thick oil (250 mg, 92%). Proton NMR was consistent with N-(p-nitrophenyl)-2-methyl-4-trifluoromethyl imidazole.

To a suspension of the above nitro compound (1 mmol) in MeOH (6 mL) and acetic acid (1 mL) was added 10% Pd/C (75 mg) followed by ammonium formate (100 mg) and the reaction mixture was stirred for 15 min. The catalyst was filtered off, the MeOH evaporated and the residue taken up in 10% $NaHCO_3$ (25 mL), extracted with $CH_2Cl_2$ (2×50 mL), the combined extracts washed with brine, dried over anhydrous $Na_2SO_4$ and concentrated to give a reddish brown oil which solidified on standing to the corresponding amine.

Coupling of the above amine with 4-chlorobenzoic acid was carried out by the same method as described in Example 1 to give the title compound. The title compound was purified by flash column chromatography over silica gel eluting with 8% EtOAc/CH$_2$Cl$_2$ and a fraction with Rf 0.25 collected and final purification was carried out by crystallization in hexane/benzene. The yield for the final two steps was 80%. Mp 194–195° C.; $^1$H NMR (DMSO-d$_6$) δ2.31 (3H, s), 7.51 (2H, d, J=9 Hz), 7.63 (2H, d, J=9 Hz), 7.94–8.02 (5H, m), 10.55 (1H, s)); $^{19}$F NMR (CDCL3) δ–61.5 (s).

EXAMPLE 3
Synthesis of N-[4-(1-methyl-4-trifluoromethylimidazol-2-yl)]phenyl]4-chlorobenzamide (Methods L and A)

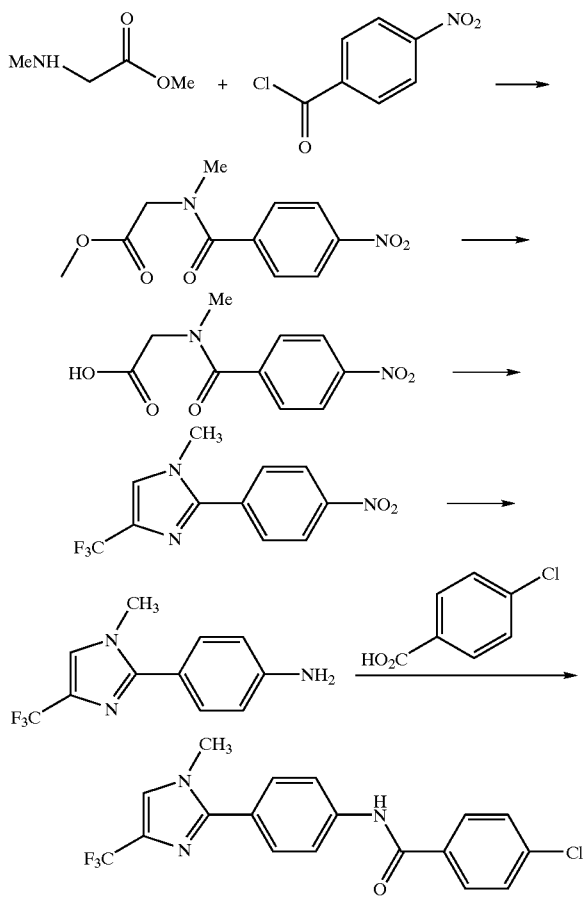

4-Nitrobenzoyl chloride (3.71 g, 20 mmol) was added to a stirred solution of sarcosine methyl ester hydrochloride (2.8 g, 20 mmol) and N-methylmorpholine (4.6 mL, 42 mmol) in CH$_2$Cl$_2$ (20 mL) and the mixture was stirred overnight at room temperature for 16 hr. The reaction mixture was diluted with CH$_2$Cl$_2$ (200 mL), washed with 1N H$_2$SO$_4$ (3×50 mL), 10% NaHCO$_3$ (3×50 mL), water (3×50 mL), dried over anhydrous Na$_2$SO$_4$ and concentrated to give a light yellow, thick oil which solidified on standing (3.6 g, 72%).

Lithium hydroxide (1.23 g, 30 mmol) in 25 mL water was added to a solution of the above sarcosine derivative (3.6 g, 14.3 mmol) in MeOH (50 mL) and the mixture was stirred at room temperature for 1 hr. The MeOH was evaporated and the aqueous residue acidified with 1N H$_2$SO$_4$, extracted with EtOAc (3×75 mL), the combined extracts washed with brine (3×25 mL), dried over anhydrous Na$_2$SO$_4$ and concentrated to give a light cream-colored solid (3 g, 88%).

Trifluoroacetic anhydride (2.12 mL, 15 mmol) was added to a suspension of the above glycine derivative (1.19 g, 5 mmol) in CH$_2$Cl$_2$ and the reaction was stirred at room temperature for 2 hr. The residue obtained after evaporation of excess reagents was triturated with ether to give a reddish yellow solid. This solid was taken up in DMF (20 mL) and ammonium acetate (0.77 g, 10 mmol) was added and the mixture heated at 70° C. for 2 hr. The DMF was evaporated under vacuum and the residue taken up in ether and cooled on ice. The precipitated solid was filtered and washed with cold ether to give a light brownish solid (0.87 g, 60%).

The above intermediate (2 mmol) was reacted with phosphorous oxychloride and pyridine as described in Example 2 and worked up in analogous fashion to give quantitative yield of 1-methyl-2-(p-nitrophenyl)-4-trifluoromethyl imidazole as a light brown solid. Reduction of the nitro group and coupling of the resulting amine to 4-chlorobenzoic acid to give the title compound was carried out as described in Example 2. The yield for the two steps was 80%.

Purification was carried out by flash column chromatography over silica gel eluting with 8% EtOAc/CH$_2$Cl$_2$ and the fraction with Rf 0.26 was collected and crystallized from benzene. Mp 221–223° C.; $^1$H NMR (DMSO-d$_6$) δ3.81 (3H, s), 7.63 (2H, d, J=9 Hz), 7.72 (2H, d, J=9 Hz), 7.92 (3H, d, J=9 Hz), 8.0 (2H, d, J=9 Hz), 10.51 (1H, s)); $^{19}$F NMR (CDCL3) δ–61.3 (s).

Assessment of Biological Properties
IL-2 Promoter Assay

The IL-2 promoter assay measures transcriptional activation of a luciferase reporter gene which has been placed under control of the IL-2 promoter/enhancer. All the known regulatory features of the IL-2 gene are contained within a ~300 bp sequence immediately upstream of the open reading frame. The region −328 to +35 relative to the transcription start site of the IL-2 gene is obtained by RT-PCR of human genomic DNA and is subcloned into the promoterless luciferase reporter vector pGL2-Basic (Promega). The resulting construct, pIL2P-luc, and a vector containing a neomycin resistance gene, pcDNA/Neo (Invitrogen), are linearized and stably transfected into Jurkat cells (a human T-cell line) by electroporation. Following G-418 selection and dilution cloning, a cell line was established, J.1F/C6., which exhibited a strong induction of luciferase activity upon treatment with ionomycin and PMA (up to 100-fold), and potent inhibition by FK506 (IC$_{50}$=0.3 nM).

For screening compounds, the cells are pelleted by centrifugation, washed once with PBS, resuspended in RPMI (phenol red-free) containing 5% FBS, and dispensed into 96-well, white microtiter plates (Packard) at 50,000 cells/well. The cells are pre-incubated with compounds (1 μg/ml) for 15 min prior to addition of ionomycin (1 μg/ml) and PMA (10 ng/ml) in a final volume of 100 μl. Following a 5 hr incubation at 37° C. in a humidified incubator, 100 μl of Luc-Lite lysis buffer/luciferase assay buffer (Promega) is added and luminescence measured using a Packard Top-Count scintillation counter/luminometer.

The synthetic examples and were screened in this assay and had IC$_{50}$s below 10 microM While we have described a number of embodiments of this invention, it is apparent that our basic constructions may be altered to provide other embodiments which utilize the products and methods of this invention. Therefore, it will be appreciated that the scope of this invention is to be defined by the appended claims, rather than by the specific embodiments that have been presented herein by way of example.

What is claimed is:

1. A compound of Formula Ia

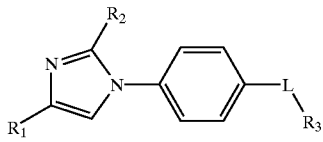

wherein:
- $R_1$ and $R_2$, which are the same or different, are $CF_3$; halogen; CN; branched or unbranched $C_{1-8}$ alkyl; branched or unbranched $C_{1-8}$ alkenyl; $C_{3-8}$ cycloalkyl optionally substituted with OH, CN, or methoxy; $C_{1-8}$ alkoxy; $C_{1-4}$ alkyloxyalkyl; $C_{1-8}$ alkylthio; $C_{1-4}$ alkylthioalkyl; $C_{1-8}$ dialkylamino; $C_{1-4}$ dialkylaminoalkyl; $CO_2R_4$ where $R_4$ is $C_{1-4}$ alkyl or $C_{1-4}$ alkenyl optionally substituted with carbocyclyl or heterocyclyl; or aryl or heterocyclyl connected to the imidazole in any position that makes a stable bond wherein the aryl or the heterocyclyl thereof is optionally substituted with halogen, $C_{1-4}$ alkyl, $C_{1-4}$ alkenyl, CN, $Me_2N$, $CO_2Me$, OMe, aryl, heterocyclyl, or $R_4$;
- L is —NHC(O)—; —NHC(O)O—; —NHC(O)C(O)—; —NHC(S)—; —NH—; —NHC(O)NH—; —NHC(S)NH—; —NHCH$_2$—; —NHCH($R_5$)—, wherein $R_5$ is H, CN, $C_{1-6}$ alkyl, $C_{1-6}$ alkyloxyalkyl, $C_{1-6}$ alkylthioalkyl, $C_{1-6}$ alkylsulfinylalkyl, $C_{1-6}$ alkylsulfonylalkyl, $C_{3-6}$ cycloalkyl, heterocyclyl, or aryl optionally substituted with a halogen, $C_{1-4}$ alkyl, CN, $Me_2N$, $CO_2Me$, or OMe; or —NHC($R_5$)-lower alkyl; and
- $R_3$ is $C_{1-8}$ alkyl; $C_{1-8}$ alkyloxy; $C_{1-8}$ alkylthio; $C_{1-8}$ alkylamino; $C_{1-4}$ alkoxyalkyl; $C_{1-4}$ alkylthioalkyl; $C_{1-4}$ alkylaminoalkyl; $C_{1-4}$ dialkylaminoalkyl; —$CO_2R_6$; —$N(R_6)_2$; —$NH(R_6)$; —$C(O)R_6$; —$OR_6$; $S(O)_nR_6$, wherein n is 0, 1, or 2; —$SO_2NHR_6$; —$SO_2N(R_6)_2$; or carbocyclyl or heterocyclyl, wherein the carbocyclyl or heterocyclyl thereof is optionally substituted with one or more of the following:
  - halogen, —CN, —$NO_2$, —$SO_2NH_2$, $CF_3$, $OCF_3$, $OC_{1-4}$ alkyl, $OC_{3-5}$alkenyl, $CO_2C_{1-2}$alkyl, SMe, $NMe_2$, $R_6$, or $O(CH_2)_pR_7$, where p is 3 or 4 and $R_7$ is CN, $CO_2Me$, 2-(1,3-dioxolanyl), OH, or $OC_6H_5$, wherein:
- $R_6$ is phenyl, heterocyclyl, $C_{3-6}$ cycloalkyl, $C_{1-6}$ alkyl, $C_{2-6}$ alkenyl, $C_{1-6}$ alkyloxyalkyl, $C_{1-6}$ alkylthioalkyl, $C_{1-6}$ alkylsulfinylalkyl, $C_{1-6}$ alkylsulfonylalkyl, or $C_{2-6}$ alkynyl and $R_6$ is optionally substituted with halogen, —OH, alkyloxy, —CN, —COO-lower alkyl, —CONH-lower alkyl, —CONH-lower alkyl, —CON(lower alkyl)$_2$, dialkylamino, phenyl, or heterocyclyl,
- each aryl group is independently a phenyl group or naphthyl group,
- each carbocyclyl group is independently a stable saturated or unsaturated, aromatic or non-aromatic, 3 to 8 membered monocyclic or 7 to 11 membered bicyclic radical, and
- each heterocyclyl group is independently a stable saturated or unsaturated, aromatic or non-aromatic, 5 to 8 membered monocyclic or 8 to 11 membered bicyclic heterocycle radical including 1 to 4 heteroatoms selected from the group consisting of nitrogen, oxygen, and sulfur, and is optionally benzo- or pyridofused if monocyclic, or a pharmaceutically acceptable derivative thereof.

2. The compound as recited in claim 1, wherein:
- $R_1$ is straight-chained, branched, or cyclo-$C_{3-8}$ alkyl, alkenyl, or alkynyl; $C_{1-3}$ alkyloxyalkyl; $C_{1-5}$ alkyloxy; $C_{1-3}$ alkylthioalkyl; $C_{1-5}$ alkylthio; $CF_3$; or heterocyclyl or aryl optionally substituted with halogen, $C_{1-4}$ alkyl, CN, alkoxy, or $Me_2N$;
- $R_2$ is halogen; Me; Et; $CF_3$; CN; cyclopropyl; vinyl, SMe, OMe, heterocyclyl or aryl optionally substituted with halogen, $C_{1-4}$ alkyl, CN, alkoxy, or $Me_2N$;
- L is —NHC(O)—, —NH—, —NHC(O)NH, or —NHCH($R_5$)—, wherein $R_5$ is H, $C_{1-4}$ alkyl, or CN; and
- $R_3$ is $C_{1-6}$ alkyl; $C_{1-4}$ alkyloxyalkyl; $C_{1-4}$ alkylthioalkyl; cyclohexyl; cyclopentyl; indanyl; indolyl; phenyl; thienyl; naphthyl; isoxazolyl or pyridyl; optionally substituted with one or more halogen, —CN, —$NO_2$, $SO_2NH_2$, or $R_6$ (where $R_6$ is $C_{1-6}$ alkyl, $C_{2-6}$ alkenyl, $C_{1-6}$ alkyloxyalky, $C_{1-6}$ alkylthioalkyl, or $C_{2-6}$ alkynyl) or $R_6$ optionally substituted with OH, CN, —COO-lower alkyl, —CONH-lower alkyl, —CON(lower alkyl)$_2$, dialkylamino, or heterocyclyl; or
- $R_3$ is $CO_2R_6$; —$N(R_6)_2$; —$NH(R_6)$; —$C(O)R_6$; —$OR_6$; $S(O)_nR_6$ where n is 0, 1, or 2; —$SO_2NHR_6$, or —$SO_2N(R_6)_2$.

3. The compound according to claim 1, wherein:
- $R_1$ is Et, i-Pr, n-Pr, t-Bu, cyclopentyl, $CF_3$, —OEt, MeOCH$_2$—, 2- or 3-tetrahydrofuranyl, 2-, 3-, or 4-pyridyl, 2-furanyl, or 2-thiazolyl;
- $R_2$ is CN, $CF_3$, Cl, Me, Et, SMe, cyclopropyl, vinyl, or 2-furanyl;
- L is —NHC(O)—, —NH—, or —NHCH$_2$—; and
- $R_3$ is a phenyl ring optionally substituted with one to three groups selected from $C_{1-3}$ alkyl, chloro, fluoro, $CF_3$, $OC_{1-4}$alkyl, $OC_{3-5}$alkenyl, $CO_2C_{1-2}$alkyl, SMe, CN, $NO_2$, $NMe_2$ and $O(CH_2)_pR_7$, where p is 3 or 4 and $R_7$ is CN, $CO_2Me$, 2-(1,3-dioxolanyl), OH, or $OC_6H_5$; 1- or 2-indanyl; 2-tetrahydropyranyl; or a heterocycle selected from the group consisting of 2-thienyl, 3-furanyl, 3- or 4-pyridyl; 4-isoxazolyl; 1-isoquinolinyl; 2-indolyl; 2-benzothienyl or 4-pyrazolyl optionally substituted with one to three groups selected from Cl, Br, Me, CN, $CF_3$, $OCF_3$, $NO_2$, or $O(CH_2)_pR_7$, where p is 3 or 4 and $R_7$ is CN, $CO_2Me$, 2-(1,3-dioxolanyl), OH, or $OC_6H_5$; $C_{5-6}$ alkyl, $C_{5-6}$cycloalkyl; or cyclohexenyl.

4. The compound according to claim 1, wherein:
- $R_1$ is i-Pr, $CF_3$, 3-pyridyl or 4-pyridyl;
- $R_2$ is CN, $CF_3$, Cl, Me, SMe or Et;
- L is —NHC(O)—, —NH—, or —NHCH$_2$—; and
- $R_3$ is a phenyl ring optionally substituted with $O(CH_2)_3R_8$, wherein $R_8$ is CN, OH, or 2-(1,3-dioxolanyl); $OC_{3-4}$alkyl; $O(CH_2)_4OH$; 1-pentenyl, one to three groups selected from Me, Cl, F, and CN; 3-pyridyl optionally substituted in the 6-position with $O(CH_2)_2$OEt or $O(CH_2)_3R_8$, where $R_8$ is CN, OH or 2-(1,3-dioxolanyl); 4-pyridinyl optionally substituted with a chlorine, 2-thienyl optionally substituted with Me or Br, 3,5-dimethyl-4-isoxazolyl, 1-methyl-2-indolyl, cyclopentyl, cyclohexyl, 1-indanyl or n-pent-3-yl.

5. A compound selected from the group consisting of:

(a) N-[4-(2-Ethyl-4-pyridin-3-yl-imidazol-1-yl)phenyl]pyridine-3-carboxamide;
(b) (2-Chloro-6-fluorobenzyl)-[4-(2-ethyl-4-pyridin-3-yl-imidazol-1-yl)phenyl]amine;

(c) (2-Methylbenzyl)-[4-(2-ethyl-4-pyridin-3-yl-imidazol-1-yl)phenyl]amine;
(d) [6-(3-Cyanopropoxy)pyridin-3-ylmethyl]-[4-(2-cyano-4-pyridin-3-yl-imidazol-1-yl)phenyl]amine;
(e) [6-(3-[1,3]Dioxolan-2-ylpropoxy)pyridin-3-ylmethyl]-[4-(2-cyano-3-pyridin-4-yl-imidazol-1-yl)phenyl]amine;
(f) N-[4-(2-Ethyl-4-pyridin-3-yl-imidazol-1-yl)phenyl]-1-methylindole-2-carboxamide;
(g) (2-Chloro-6-fluorobenzyl)-[4-(2-cyano-4-pyridin-3-yl-imidazol-1-yl)phenyl]amine;
(h) [4-(2-Cyano-4-pyridin-3-yl-imidazol-1-yl)phenyl]-(2,6-dimethylbenzyl)-amine;
(i) (2-Chloro-6-methylbenzyl)-[4-(2-cyano-4-pyridin-3-yl-imidazol-1-yl)phenyl]amine;
(j) [4-(2-Cyano-4-pyridin-3-yl-imidazol-1-yl)phenyl]-(2-indanylmethyl)amine;
(k) [4-(2-Ethyl-4-pyridin-3-yl-imidazol-1-yl)phenyl]-(2-indanylmethyl)amine;
(l) [4-(2-Ethyl-4-pyridin-3-yl-imidazol-1-yl)phenyl]-(2-fluoro-6-methylbenzyl)amine;
(m) 4-(3-Cyanopropoxy)-N-[4-(2-cyano-4-pyridin-3-yl-imidazol-1-yl)phenyl]benzamide;
(n) N-[4-(2-Cyano-4-pyridin-3-yl-imidazol-1-yl)phenyl]-4-(3-[1,3]dioxolan-2-yl-propoxy)benzamide;
(o) [4-(3-Cyanopropoxy)benzyl]-[4-(2-ethyl-4-pyridin-3-yl-imidazol-1-yl)phenyl]amine;
(p) [4-(3-Cyanopropoxy)benzyl]-[4-(2-cyano-4-pyridin-3-yl-imidazol-1-yl)phenyl]amine;
(q) N-[4-(4-Methyl-2-phenylimidazol-1-yl)]phenyl]4-chlorobenzamide;
(r) N-[4-(2-Methyl-4-trifluoromethylimidazol-1-yl)]phenyl]4-chlorobenzamide;
(s) N-[4-(1-Methyl-4-trifluoromethylimidazol-2-yl)]phenyl]4-chlorobenzamide; and
(t) N-[4-(1-Ethyl-4-pyridin-3-yl-imidazol-2-yl)]phenyl]4-chlorobenzamide.

6. A method of treating an inflammatory disease which comprises administering to a patient in need of such treatment a therapeutically effective amount of a compound as recited in claim 1.

7. A method of treating an autoimmune disease which comprises administering to a patient in need of such treatment a therapeutically effective amount of a compound as recited in claim 1.

8. A method of treating a disease in which excessive production of IL-2 is a contributing factor, which comprises administering to a patient in need of such treatment a IL-2 production inhibiting amount of a compound as recited in claim 1.

9. A pharmaceutical composition comprising an effective amount of compound according to claim 1 and a pharmaceutically acceptable carrier or adjuvant.

10. The compound according to claim 1, wherein each heterocyclyl group is independently selected from the group consisting of: benzimidazolyl, furyl, imidazolyl, imidazolinyl, imidazolidinyl, quinolinyl, isoquinolinyl, indolyl, oxazolyl, pyridyl, pyrrolyl, pyrrolinyl, pyrazolyl, pyrazinyl, pyrimidinyl, pyridazinyl, quinoxolyl, piperidinyl, morpholinyl, thiomorpholinyl, furyl, thienyl, triazolyl, thiazolyl, β-carbolinyl, tetrazolyl, thiazolidinyl, benzofuranoyl, thiomorpholinyl sulfone, benzoxazolyl, oxopiperidinyl, oxopyrrolidinyl, oxoazepinyl, azepinyl, isoxazolyl, tetrahydropyranyl, tetrahydrofuranyl, thiadiazoyl, benzodioxolyl, tetrahydrothiophenyl, and sulfolanyl.

11. The compound according to claim 2, wherein each heterocyclyl group is independently selected from the group consisting of: benzimidazolyl, furyl, imidazolyl, imidazolinyl, imidazolidinyl, quinolinyl, isoquinolinyl, indolyl, oxazolyl, pyridyl, pyrrolyl, pyrrolinyl, pyrazolyl, pyrazinyl, pyrimidinyl, pyridazinyl, quinoxolyl, piperidinyl, morpholinyl, thiomorpholinyl, furyl, thienyl, triazolyl, thiazolyl, β-carbolinyl, tetrazolyl, thiazolidinyl, benzofuranoyl, thiomorpholinyl sulfone, benzoxazolyl, oxopiperidinyl, oxopyrrolidinyl, oxoazepinyl, azepinyl, isoxazolyl, tetrahydropyranyl, tetrahydrofuranyl, thiadiazoyl, benzodioxolyl, tetrahydrothiophenyl, and sulfolanyl.

12. A pharmaceutical composition comprising an effective amount of compound according to claim 10 and a pharmaceutically acceptable carrier or adjuvant.

13. A pharmaceutical composition comprising an effective amount of compound according to claim 11 and a pharmaceutically acceptable carrier or adjuvant.

14. A pharmaceutical composition comprising an effective amount of compound according to claim 2 and a pharmaceutically acceptable carrier or adjuvant.

15. A pharmaceutical composition comprising an effective amount of compound according to claim 3 and a pharmaceutically acceptable carrier or adjuvant.

16. A pharmaceutical composition comprising an effective amount of compound according to claim 4 and a pharmaceutically acceptable carrier or adjuvant.

17. A pharmaceutical composition comprising an effective amount of compound according to claim 5 and a pharmaceutically acceptable carrier or adjuvant.

* * * * *